United States Patent [19]

Kabil

[11] 3,936,352

[45] Feb. 3, 1976

[54] PROCESS FOR THE PRODUCTION OF CITRIC ACID

[75] Inventor: Adel J. Kabil, Vienna, Austria

[73] Assignee: Aktiengesellschaft Jungbunzlauer Spiritus- und Chemische Fabrik, Scharzenbergplatz, Austria

[22] Filed: Oct. 12, 1973

[21] Appl. No.: 406,130

Related U.S. Application Data

[63] Continuation-in-part of Ser. No. 146,555, May 24, 1971, abandoned.

[30] Foreign Application Priority Data

June 1, 1970 Austria............................ 4891/70

[52] U.S. Cl................. 195/36 R; 195/139; 195/114
[51] Int. Cl.²............................................ C12D 1/04
[58] Field of Search............... 195/36 R, 47, 35, 142, 195/139

[56] References Cited
UNITED STATES PATENTS

| | | | |
|---|---|---|---|
| 1,524,233 | 1/1925 | Berrigan ................................ | 426/32 |
| 2,394,031 | 2/1946 | Waksman et al. ................. | 195/36 R |
| 2,883,329 | 4/1959 | Vergnaud et al. ................. | 195/36 R |
| 2,910,409 | 10/1959 | Fried et al.......................... | 195/36 R |
| 3,075,888 | 1/1963 | Achorn et al....................... | 195/142 |
| 3,290,227 | 12/1966 | Batti.................................. | 195/36 R |
| 3,349,005 | 10/1967 | Batti.................................. | 195/36 R |

OTHER PUBLICATIONS

Chem. Abstracts 66:17989q.

*Primary Examiner*—Lionel M. Shapiro
*Assistant Examiner*—Thomas G. Wiseman
*Attorney, Agent, or Firm*—Browne, Beveridge, DeGrandi & Kline

[57] ABSTRACT

The invention relates to a process for the production of citric acid which comprises subjecting a carbohydrate-containing material to a submerged fermentation with a citric acid producing strain of Aspergillus niger in the presence of metals such as iron and copper.

The object of the invention is to provide a process in which control of the trace metal content can be achieved in an economic and convenient manner.

The improvement according to the invention comprises carrying out said fermentation in the presence of refined steel which in addition to iron and copper contains at least one component selected of the group comprising chromium, manganese, nickel, molybdenum, niobium and titanium.

6 Claims, No Drawings

PROCESS FOR THE PRODUCTION OF CITRIC ACID

CROSS-REFERENCE TO RELATED APPLICATIONS

This application is a continuation-in-part application of U.S. application Ser. No. 146,555 filed May 24, 1971, now abandoned, on which this application relies for priority. This patent application Ser. No. 146,555 filed May 24, 1971 is incorporated herein by reference.

BACKGROUND OF THE INVENTION

The invention relates to a process for the production of citric acid which comprises subjecting a carbohydrate-containing material to a submerged fermentation with a citric acid producing strain of Aspergillus niger in the presence of metals such as iron and copper.

It is known that trace amounts of various metals such as iron, copper and zinc have a vital effect on the physiology of the organism used in the fermentation process. The metals not only promote the growth of the organism, they also have an effect on the yield of citric acid obtained from the carbohydrate-containing material used. It is known that although iron is required for the growth of microorganisms including Aspergillus niger, the presence of this metal can have a very detrimental effect on the citric acid yield obtained if this metal is present in the fermentation medium in larger than trace amounts. Various attempts have been made to remove surplus amounts of this metal e.g. by ion exchange, precipitation or complexation processes, also when using carbohydrate-containing materials which contain relatively small amounts of this metal. It has also been found that copper or morpholine can be used to counteract the detrimental effects of surplus amounts of iron.

It is an object of the invention to provide a process in which control of the trace metal content can be achieved in an economic and convenient manner.

SUMMARY OF THE INVENTION

According to the invention the improvement comprises carrying out said fermentation in the presence of refined steel which in addition to iron and copper contains at least one component selected of the group comprising chromium, manganese, nickel, molybdenum, niobium and titanium.

In this, the refined steel acts as the source of trace elements whereby an optimum concentration of trace metals in the fermentation mash and thereby a high yield of citric acid is obtained.

This effect is surprising as according to conventional practices the use of refined steel in the production of citric acid is avoided or at least contact between the fermentation solution and the refined steel is reduced to a minimum by coating the fermenting vessels e.g. with rubber or by using fermenting vessels which are made of non-ferrous metals such as titanium, aluminum or glass.

DETAILED DESCRIPTION

By way of exemplification, not by way of limitation, the invention will be more readily understood by the description of the preferred embodiment which follows. The invention comprises preparing citric acid by subjecting a carbohydrate-containing material to a submerged fermentation with a citric acid producing strain of Aspergillus niger in the presence of refined steel.

Suitable for the process according to the invention are the stainless steels, set forth on page 159 and 151 of Nachschlagewerk Stahlschlussel, 8., Edition 1968, Publication and Distribution of Verlagstahlschüssel Wegst Kg, West Germany, identified as steels Standard No. 1.4505 and 1.4586. The Publication Stahlschlussel, identified above, at pages 150 and 151 is incorporated herein by reference. Two other steels listed in the Stahlschlussel publication at pages 150 and 151, the steels identified as Standard No. 1.4571 and 1.4541, serve as comparisons. These steels will be referred to hereafter by their numbers 1.4505, 1.4586, 1.4541 and 1.4571.

The exact compositions of these steels are set forth in Table II. Table II corresponds substantially to Table II of the co-pending parent application Ser. No. 146,555 filed May 24, 1971, as to the compositions of the refined steels useful in this invention. The compositions set forth in Table II are expressly recited at pages 150 and 151 of the Stahlschlüssel reference incorporated herein by reference. As is obvious, values of the components set forth in Table II are proportions, rather than ranges.

The steels 1.4505 and 1.4586 contain as components, in addition to iron and carbon, silicon, manganese, chromium, molybdenum, nickel, copper and niobium. As set forth in Table II, the components in the steels 1,4505 have values of 2% manganese, about 0.07% carbon, about 1% silicon, 17.5% chromium, 2.25% molybdenum, 20% nickel, 2% copper and niobium in an amount eight times greater than that of the carbon component. 1.4586 contains about 0.07% carbon, about 1% silicon, 2% manganese, 18,0% chromium, 2.75% molybdenum, 22.0% nickel, 2% copper and an amount of niobium eight times greater than that of carbon. Steel 1.4541 contains about 0.10% carbon and about 1% silicon, as well as manganese, chromium, nickel and titanium. Steel 1.4571 contains about 0.10% carbon, about 1% silicon, as well as manganese, chromium, molybdenum, nickel and titanium. The titanium component of steels 1.4571 and 1.4541 is said to be present in an amount five times greater than that of carbon, as is set forth in Table II.

It is of advantage to adjust the pH value to approximately 2.8 after addition of the nutrient solution. It is useful to follow this up with sterilization at temperatures of 100°C. or above and, after cooling off, the addition of e.g. the refined steel and its coming into contact with the nutrient solution, respectively, if parts of the construction of the fermenter, feeder lines, cooling coils or the entire fermenter are made of this steel.

Then, the solution is inoculated with the spores of Aspergillus niger and fermentation is carried out at temperatures of approximately 30°– 32°C. The improvement in yield in submerged fermentation in the presence of refined steel as compared to fermentation without the addition of metal is illustrated by the following examples:

EXAMPLE 1

A decationized sugar solution of 20% by weight per volume was adjusted to a pH value of 2.8 after the addition of nutrient salts.

80 ml each of the solution mentioned above were placed in 4 vibrator flasks, sterilised in streaming steam for half an hour at 100°C. and cooled off to 30°C. In two of the vibrator flasks, a piece of sterilized stainless steel 1.4505 or 1.4586, respectively, with a surface ratio of 1.2 cm²/100 ml was introduced into the sugar-containing solution. The other two vibrator flasks were left without metal addition.

All 4 flasks were inoculated with a suspension of spores of Aspergillus niger and subjected to vibration for about 12 days at a temperature of 30°– 32°C. The results of fermentation are evident from the following table.

Table I :

| Test | Addition of Refined Steel | Fermentation Time in Days | Citric Acid Yield in % |
|---|---|---|---|
| 1 | – | 12 | 35.5 |
| 2 | – | 12 | 30.1 |
| 3 | + | 11 | 61.1 |
| 4 | + | 13 | 59.8 |

EXAMPLE 2

11 liters of a sugar solution partially purified by decationization with a content of 25% by weight per volume of sugar were adjusted to a pH value of 2.8 after the addition of nutrient salts, sterilized in streaming steam at a temperature of 100°C. cooled off to 30°C. and then transferred to a glass fermenter with a diameter of 150 mm and a height of 1000 mm under sterile conditions. Ventilation was effected by a distributor pipe at the bottom of the fermenter. The fermenter contained a piece of refined steel of the type 1.4541 with a surface area of 131 cm². The fermentation solution was inoculated with Aspergillus niger at a temperature of 30°C. After a fermentation period of 14 days, 614 g citric acid crystals, were obtained, which corresponds to a yield of 22.3%.

EXAMPLE 3 :

The fermentation solution treated as described in Example 2 was put into a fermenter as described in Example 2 containing a piece of refined steel of the type 1.4571 with a surface area of 131 cm². The fermentation solution was inoculated at a temperature of 30°C. with spores of Aspergillus niger and at the same time 11 mg of potassium hexacyano ferrate-II were added. On the third day, 6.6 mg., on the fifth day, 4.4 mg and on the eighth day, 3.3 mg. of potassium hexacyano ferrate-II were added. After a fermentation period of 12 days, 1.254 g of citric acid crystals were obtained, which corresponds to a yield of 45.6%.

EXAMPLE 4

The fermentation solution treated as described in Examples 2 and 3 was put into a fermenter as described in Example 2 containing a piece of refined steel of the type 1.4505 with a surface area of 131 cm². The inoculation with Aspergillus niger was effected. The fermentation period was terminated after 10 days. 2.456 g of citric acid crystals were obtained, which corresponds to a yield of 89.3%.

EXAMPLE 5

The fermentation solution treated according to the preceding examples was placed into a fermenter as described in Example 2 which had been provided with a piece of refined steel of the type 1.4586 with a surface area of 131 cm². After inoculation with the spores of Aspergillus niger, 11 mg. of potassium hexacyano ferrate-II were added to the fermenting mash on the first day, 3.3 mg. on the fifth day and 2.2 mg. on the seventh day. After a fermentation period of 10 days, 2.480 g of citric acid crystals were obtained, which corresponds to a yield of 90.18%.

Table II :

| Examples | Refined Steel added, Standard No. | Fermentation Time in Days | Citric Acid Yield in % |
|---|---|---|---|
| 2 | 1.4541 | 14 | 22.3 |
| 3 | 1.4571 | 12 | 45.6 |
| 4 | 1.4505 | 10 | 89.3 |
| 5 | 1.4586 | 10 | 90.18 |

Composition of the Steels used in the Examples:

| Steels | C | Si | Mn | Cr | Mo | Ni | Cu | others |
|---|---|---|---|---|---|---|---|---|
| 1.4505 | 0.07% | 1% | 2% | 17.5% | 2.25% | 20.0% | 2% | Nb 8×C |
| 1.4586 | 0.07% | 1% | 2% | 18.0% | 2.75% | 22.0% | 2% | Nb 8×C |
| 1.4541 | 0.10% | 1% | 2% | 18.0% | – | 10.0% | – | Ti 5×C |
| 1.4571 | 0.10% | 1% | 2% | 17.5% | 2.25% | 11.5% | – | Ti 5×C |

I claim:

1. In a process for the production of citric acid which comprises subjecting a decationized sugar solution to submerged fermentation with a citric acid producing strain of Aspergillus niger in the presence of metals such as iron and copper, the improvement which comprises providing a decationized sugar solution with a pH of about 2.8 and carrying out said fermentation in the presence of a refined steel which in addition to iron and copper contains at least one component selected from the group consisting of carbon, silicon, manganese, chromium, molybdenum, nickel, niobium and titanium, wherein the amount of copper in the steel is 2%.

2. The process of claim 1, wherein the refined steel contains, in addition to iron and copper, at least one component selected from the group consisting of carbon, silicon, manganese, chromium, molybdenum, nickel and niobium.

3. The process of claim 2, wherein the refined steel contacts said nutrient solution, by the introduction of a piece of said refined steel into the nutrient solution.

4. The process of claim 1, wherein the refined steel contacts said nutrient solution, by employing a fermenter, the construction of the whole of which or the construction of parts of which require use of said refined steels.

5. In a process for the production of citric acid which comprises subjecting a decationized sugar solution to submerged fermentation with a citric acid producing strain of Aspergillus niger in the presence of metals such as iron and copper, the improvement which comprises carrying out the fermentation in the presence of a refined steel selected from the group consisting of steels containing
  a. about 1% silicon, 17.5% chromium, 2% manganese, 20% nickel, 2.25% molybdenum, 2% copper, about 0.07% carbon and an amount of niobium which is greater than 8 times the carbon content; and
  b. about 1% silicon, 18% chromium, 2% manganese 22.0% nickel, 2.75% molybdenum, 2% copper, about 0.07% carbon and an amount of niobium which is greater than 8 times the carbon content.

6. The process according to claim 5, wherein said refined steel is employed with a surface ratio of 1.2 cm²/100 ml nutrient solution.

* * * * *